US008931665B2

(12) United States Patent
Gold (10) Patent No.: US 8,931,665 B2
(45) Date of Patent: Jan. 13, 2015

(54) MULTI-COMPARTMENT APPARATUS FOR IN-SITU MIXING OF A PLURALITY OF COMPONENTS BEFORE USE

(71) Applicant: Amit Gold, Jerusalem (IL)

(72) Inventor: Amit Gold, Jerusalem (IL)

( * ) Notice: Subject to any disclaimer, the term of this patent is extended or adjusted under 35 U.S.C. 154(b) by 15 days.

(21) Appl. No.: 13/669,505

(22) Filed: Nov. 6, 2012

(65) Prior Publication Data

US 2014/0124534 A1    May 8, 2014

(51) Int. Cl.

| | | |
|---|---|---|
| *B67D 7/74* | (2010.01) | |
| *B67D 7/70* | (2010.01) | |
| *B67D 7/06* | (2010.01) | |
| *B67D 7/60* | (2010.01) | |
| *B67D 7/78* | (2010.01) | |
| *B01F 15/02* | (2006.01) | |
| *B65D 25/08* | (2006.01) | |
| *B65D 81/32* | (2006.01) | |
| *A61M 5/24* | (2006.01) | |
| *A61M 5/315* | (2006.01) | |
| *B01F 13/00* | (2006.01) | |
| *B01F 15/00* | (2006.01) | |

(52) U.S. Cl.
CPC ............ *B01F 15/0206* (2013.01); *B65D 25/08* (2013.01); *B65D 81/3222* (2013.01); *B65D 81/3255* (2013.01); *A61M 5/2448* (2013.01); *A61M 5/31596* (2013.01); *B01F 13/0023* (2013.01); *B01F 15/00512* (2013.01); *B01F 15/0212* (2013.01)
USPC .......... 222/129; 222/136; 222/386; 222/145.5

(58) Field of Classification Search
USPC ......... 222/129, 325, 326, 327, 137, 389, 386, 222/386.5, 189.11, 136, 145.1, 145.4, 222/145.5, 145.6, 145.7, 145.8, 95; 401/132, 40, 41, 196, 133, 200; 206/219; 604/82, 83, 84, 85, 86, 87, 604/88, 89, 90, 91, 92, 181, 187, 184, 200
See application file for complete search history.

(56) References Cited

U.S. PATENT DOCUMENTS

| | | | | |
|---|---|---|---|---|
| 3,370,754 A | * | 2/1968 | Cook et al. ..................... | 222/132 |
| 3,682,174 A | * | 8/1972 | Cohen .............................. | 604/90 |
| 3,684,136 A | * | 8/1972 | Baumann ....................... | 222/386 |
| 3,739,947 A | * | 6/1973 | Baumann et al. ............. | 222/136 |
| 3,749,084 A | * | 7/1973 | Cucchiara ...................... | 600/575 |
| 3,881,484 A | * | 5/1975 | Gidcumb, Jr. .................. | 604/89 |

(Continued)

FOREIGN PATENT DOCUMENTS

WO     WO 99/20562     4/1999

*Primary Examiner* — Kevin P Shaver
*Assistant Examiner* — Stephanie E Williams
(74) *Attorney, Agent, or Firm* — Daniel J. Swirsky; AlphaPatent Associates Ltd.

(57) ABSTRACT

A multi-compartment syringe apparatus (500) for in-situ mixing of a plurality of products before use, the apparatus comprising: a tube; a hollowed flexible plunger (530); a one way filter piston (514), connected to the plunger (530), the piston confining a first compartment (502) at a side of a needle (540) of the apparatus, and a second compartment (510) at a side of the plunger, wherein the filter allowing passage of content only form the first compartment to the second compartment (510); a first product (506), stored in the first compartment (502); a second product (508), stored in a first breakable container (504) disposed in the plunger (530); thereby the second product (508) mixes with the first product (506); and the mixed products are then pushed out of the apparatus, through the needle (540).

4 Claims, 7 Drawing Sheets

(56) References Cited

U.S. PATENT DOCUMENTS

| | | | |
|---|---|---|---|
| 3,964,643 A | 6/1976 | Morane | |
| 4,055,177 A * | 10/1977 | Cohen | 604/88 |
| 4,116,240 A * | 9/1978 | Guiney | 604/89 |
| 5,568,988 A * | 10/1996 | Knox et al. | 401/40 |
| 5,630,800 A * | 5/1997 | Blank et al. | 604/82 |
| 5,743,312 A | 4/1998 | Pfeifer | |
| 6,319,225 B1 * | 11/2001 | Sugita et al. | 604/89 |
| 6,544,233 B1 * | 4/2003 | Fukui et al. | 604/191 |
| 6,645,179 B1 * | 11/2003 | Ishikawa et al. | 604/181 |
| 7,018,089 B2 | 3/2006 | Wenz | |
| 2003/0222102 A1 | 12/2003 | Cho | |
| 2009/0180923 A1 | 7/2009 | Gong | |
| 2010/0034574 A1 | 2/2010 | Zhang | |

* cited by examiner

MULTI-COMPARTMENT APPARATUS FOR IN-SITU MIXING OF A PLURALITY OF COMPONENTS BEFORE USE

FIELD OF THE INVENTION

The present invention relates generally to container apparatus and methods, and more specifically to methods and apparatus for in situ mixing of components prior to use.

BACKGROUND OF THE INVENTION

It is often desirable or necessary to store two or more components of a product separately and to mix the components shortly before use or application. In some cases, the components may react together and thus need to be stored separately, prior to use. In some cases, these components may be of a medical preparation, a food or beverage, a chemical product, a building product or the like.

In the medical field, it is also particularly desirable to mix components in single use batches, to assure consistency in the delivery of the combined components. Compositions comprising at least two of anesthetics, pain killers, antibiotics and antiseptics need to be mixed quickly in emergency medicine, for example. Orthopedic mixtures such as bone fillers and bone cements need to be mixed immediately before use, as do medical adhesives, dental adhesives and the like.

There is therefore a need to provide apparatus and methods to perform in-situ mixing of two or more components in a hygienic, sterile manner, prior to application to a patient. Likewise, many other food/beverage/chemical mixtures need to be mixed in such apparatus prior to use.

The storage and mixing apparatus should preferably store the components separately prior to mixing. Thereafter, using a simple mechanism, mixing should be relatively quick, and the apparatus should be relatively cheap.

Several prior art patent publications in the field include:

US Patent Application Publication No. US2003222102 describes a cap device for bottles, which is capable of mixing an additive contained therein with a material contained in a bottle to prepare a mixture in accordance with a simple rotating action of the cap device relative to the bottle, performed by a user, thus allowing the user to easily prepare the mixture just before taking or using the mixture. The cap device has a cap body tightened to an externally threaded mouth of the bottle, with a funnel part integrally formed in the cap body to discharge the additive from the cap body into the bottle through a lower end thereof. A cap cover is assembled with the cap body to cover an open upper end of the cap body while defining a cavity inside both the cap body and the cap cover to contain the additive in the cavity. The cap device also has a valve means for opening or closing the lower end of the funnel part of the cap body in accordance with the rotating action of the cap body relative to the externally threaded mouth of the bottle.

U.S. Pat. No. 5,743,312 describes an apparatus for combining liquid or solid components stored in containers includes a cylindrical hollow body for receiving end closures of the containers and at least one cannula for penetrating the end closures. The cannula is mounted in a cannula holder movable in the hollow body, and retainer bridges connect the cannula holder to an inner wall surface of the hollow body. The retainer bridges fracture after the cannula penetrates the end closure in the first container so that the cannula moves toward the second container to penetrate the closure in the second container. Also disclosed is a system including the apparatus, two containers, and outer packaging enclosing the containers and the hollow body.

U.S. Pat. No. 7,018,089 discloses a double syringe apparatus and method for mixing two components.

US Patent Application Publication No. US2009180923A relates to a self-mixing container with a releasable internal vessel and its usage, wherein said self-mixing container comprises a container body, a double-walled external cap and an internal vessel, and through a corresponding production line, assembling of the self-mixing container with a releasable internal vessel will be realized. The invention makes it possible to pack and seal in a cold filling process at least two different materials in one and the same container body respectively. When in use, at least two kinds of materials are mixed and formulated in one and the same container body in a rapid and automatic way, by means of relative movement of the screw-threads by which the container body, the double-walled external cap and the internal vessel are coupled with each other, and engagement of the ratchet and the pawls, without the structure of the container body being damaged, so that initial fresh active components in the materials sealed therein are preserved, and rapid formulation is achieved. Furthermore, the structure is simple, durable and has a low fabrication cost, and it can be used without great effort or time, especially can be used conveniently when carried on, and it can be broadly applied to pharmaceutical, food and beverage, chemical, farm chemical, disinfectants, or fire-fighting equipments field.

US Patent Application Publication No. US2010034574 describes a dispensing device, including inner and outer compartments for housing two different cosmetic liquid materials therein, the outer compartment secured to a cap by threading; a spring biased valve for blocking both openings of the inner and outer compartments when the device is in an inoperative position; and an outlet assembly partially fastened in the valve. An individual may unfasten and remove the cap from the device to unblock the valve, and squeeze both the outer and the inner compartments to push the cosmetic liquid materials to mix in the outlet assembly prior to dispensing out of the device.

It is therefore still desirable to provide improved storage and mixing apparatus, which are relatively inexpensive to produce, yet should provide complete and reliable isolation of the components to be mixed prior to use. The apparatus should be suitable for both liquid-powder and liquid-liquid mixes and should be relatively simple to use. The apparatus should further provide precise and accurate delivery of the mixed compositions. At least some of these objectives will be met by the inventions described herein below.

SUMMARY OF THE INVENTION

It is an object of some aspects of the present invention to provide storage and mixing apparatus for in-situ mixing of at least two components prior to use of a resultant mixture.

In some embodiments of the present invention, improved methods and apparatus are provided for in-situ mixing of at least two components prior to use of a resultant mixture.

In other embodiments of the present invention, a method and system is described for providing a syringe apparatus and method for in-situ mixing of at least two components prior to use of a resultant mixture.

There is thus provided according to an embodiment of the present invention, a multi-compartment apparatus for in-situ mixing of a plurality of components before use, the apparatus including;

a. an outer container including a first product;
b. an inner container including a second product, wherein the inner container is adapted to release the second product into the first product thereby forming a mixture; and
c. an openable aperture portion, in fluid communication with the outer container, typically including a filter, adapted to filter the mixture prior to release via the aperture.

According to some embodiments of the present invention, the first product is a first liquid.

Furthermore, according to some embodiments of the present invention, the inner container is disposed in the first liquid.

Additionally, according to some embodiments of the present invention, the second product includes a second liquid.

According to some additional embodiments of the present invention, the outer container includes at least one flexible portion.

According to some yet further embodiments of the present invention, the at least one flexible portion may be manipulated so as to break the inner container to release the second product into the first liquid thereby forming the mixture.

Furthermore, according to some embodiments of the present invention, the apparatus is a syringe.

According to some additional embodiments of the present invention, the openable aperture further includes a removable lid.

Additionally, according to some embodiments of the present invention, upon removal of the removable lid, the filtered mixture is adapted to be released from the apparatus.

Additionally, according to some embodiments of the present invention, the multi-compartment apparatus further includes a second inner containing adapted to house a third product. The third product may be a liquid or flowable solid.

There is thus provided according to another embodiment of the present invention, a method for multi-product storage and mixing in-situ before use, the method including;
a. providing a first and second product in the apparatus as described herein;
b. releasing the second product into the first product thereby forming a mixture; and optionally,
c. filtering the mixture to form a filtrate; and
d. applying at least one of the filtrate and the mixture to a destination site.

Additionally, according to some embodiments of the present invention, the filtrate is a medical product.

There is thus provided according to another embodiment of the present invention, a multi-compartment kit for in-situ mixing of a plurality of components before use, the kit including;
a) an apparatus as described herein; and
b) instructions on how to use the apparatus.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

In all the figures similar reference numerals identify similar parts.

DETAILED DESCRIPTION OF THE INVENTION

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 1:
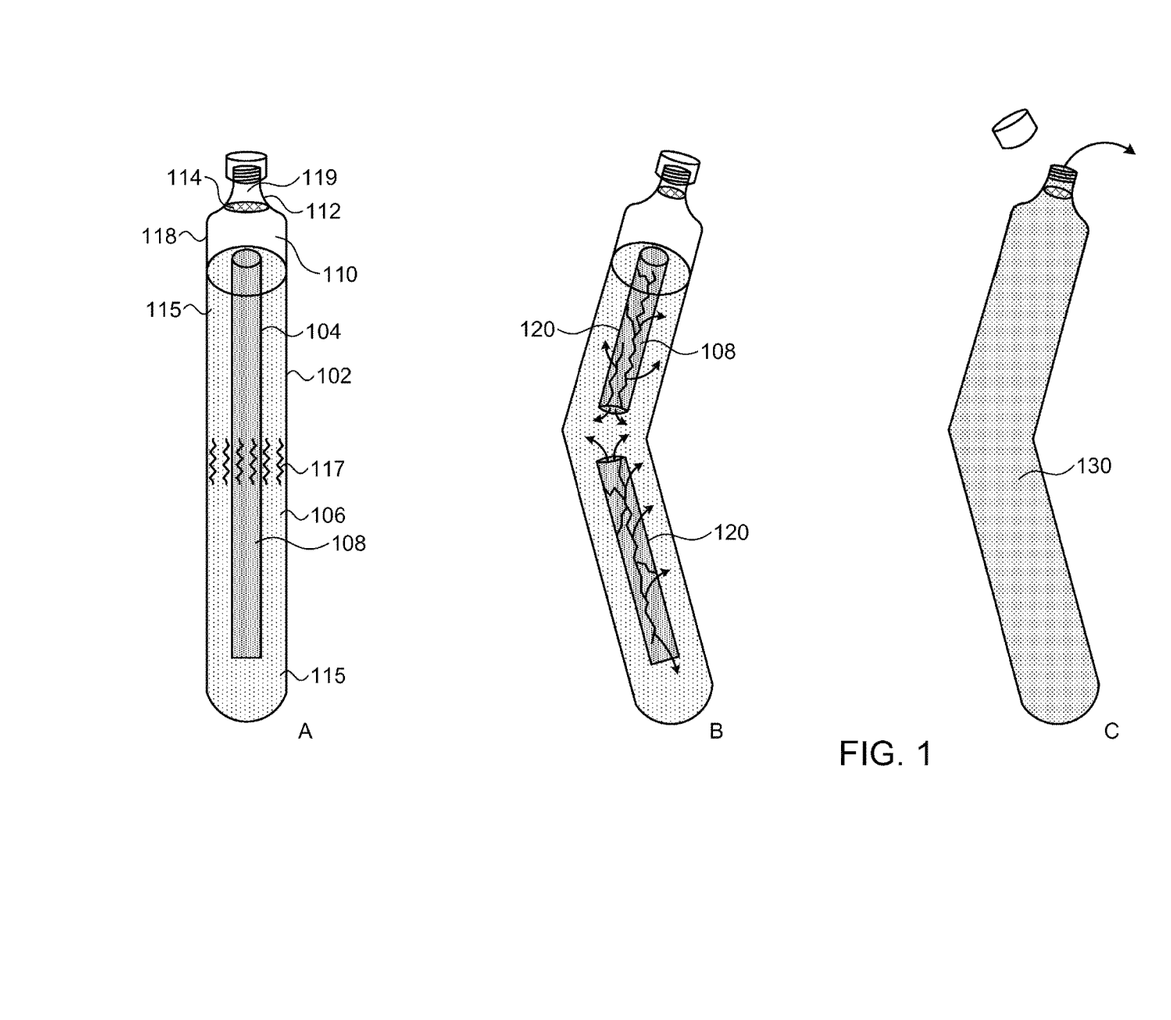
FIG. 1 is a simplified pictorial illustration of a multi-compartment apparatus for in-situ mixing of a plurality of components before use, in accordance with an embodiment of the present invention.

Reference is now made to FIG. 1, which is a simplified pictorial illustration of a multi-compartment apparatus 100 for in-situ mixing of a plurality of components before use, shown in three different positions A, B and C, respectively in accordance with an embodiment of the present invention.

Apparatus 100 comprises an external container 102, made, at least in some parts of a deformable material and contains a first liquid 106. An internal container 104 is disposed in the first liquid. The internal container comprises a second liquid 108. External container 102 typically comprises air 110 in an air portion 118. The apparatus comprises an upper portion 112 above the air portion. The upper portion comprises a filter, which allows passage of liquids from the air portion to an aperture 119, but does not allow solids to exit at aperture 119 after lid/screw cap 116 has been removed.

According to some embodiments, apparatus 100 has a flexible region 117 of made of more flexible material than the other regions 115.

According to some embodiments, regions 115 and region 117 are made of the same material of the same thickness. The material may be suitable formulations of polyethylene, polyurethane, polypropylene, polyamide or combinations thereof. According to one embodiment, the external container is made of a clear molded plastic. In some cases, coloring components or dyes will be added to the material of the outer container, if the first and/or second liquid is light sensitive, by methods well known in the art.

According to some embodiments, regions 115 and region 117 are made of the same material, but the flexible region is of a lesser thickness.

According to some embodiments, external container 102 is made of a deformable polymeric material, such as a plastic polymer or polymer blend.

As is seen in FIG. 1B, external container 102 may be bent over by pressing on two other regions 115 thereby breaking internal container 104, which is made of a stiffer, less flexible material than the external container, thereby breaking internal container 104 into pieces and releasing second liquid 108 into first liquid 106 thereby forming a mixture 130 (FIG. 1C). According to one embodiment, the internal container may be a sealed frangible glass vial. According to some further embodiments, the internal container may be made of a material, which may be glass, a glass substitute, a fragile or rigid polymer, a polymer blend or combinations thereof.

Alternatively, the user can press on a flexible region and break the internal container.

Figure 2:
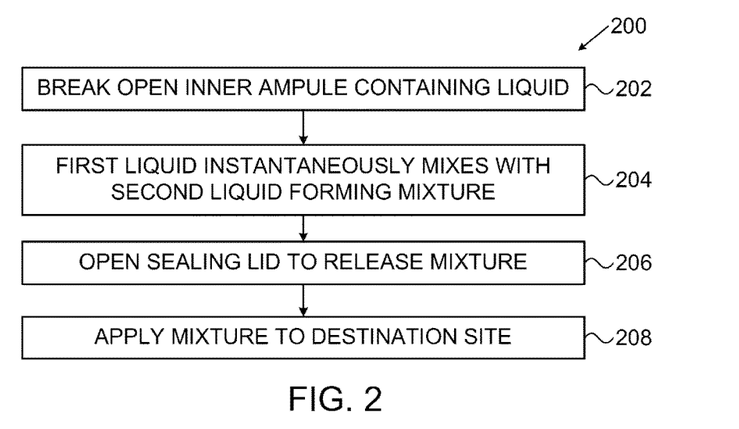
FIG. 2 is a simplified flow chart of a method for in-situ mixing of a plurality of components using the apparatus of FIG. 1, in accordance with an embodiment of the present invention.

Reference is now made to FIG. 2, which is a simplified flow chart 200 of a method for in-situ mixing of a plurality of components using the apparatus of FIG. 1, in accordance with an embodiment of the present invention.

In a first breaking step 202, the user breaks the inner container (or ampoule) by deforming the outer container from the upper and lower portions 115 or by pressing in on flexible portion 117.

In a mixing step, as shown in FIG. 1B, inner container 104 is broken into pieces 120 and thereby releases second liquid 108 into first liquid 106 thereby forming a first mixture 130. The user may additionally shake the apparatus to ensure enhanced mixing.

In an opening step 206, the user opens lid 116 (which may be a screw cap, cork, bung, lid or any other suitable lid).

In an application step 208, the mixture passes through filter 114 to ensure that no pieces 120 exit from aperture 119. The liquid mixture is then applied to the target site. This may be an external body site, a piece of furniture, it may be eaten/drunk if appropriate, or applied to the required destination site. It should be understood that the mixture may be a suspension, a liquid-gas fluid or any other liquid-like mixture.

Figure 3:
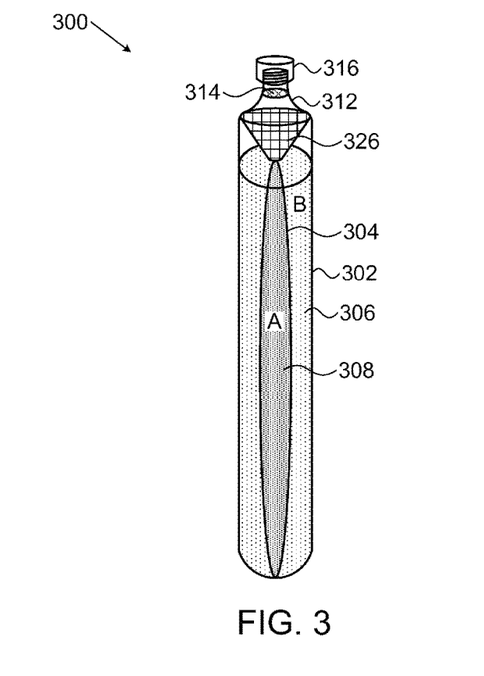
FIG. 3 is a simplified pictorial illustration of another multi-compartment apparatus, in accordance with an embodiment of the present invention.

Reference is now made to FIG. 3, which is a simplified pictorial illustration of another multi-compartment apparatus 300, in accordance with an embodiment of the present invention. Apparatus 300 comprises a netting 326 or filter disposed within an outer container 302. The netting 326 or filter is suitably disposed adjacent to an upper portion 312 of the apparatus to ensure adequate catching of pieces 120 formed upon breaking of inner container 304, in addition to a filter 314 disposed in the upper portion 312.

As was shown in FIG. 1A, in apparatus 100, the inner container was not attached to any part of the outer container. In contrast, in FIG. 4, there is seen a simplified pictorial illustration of another multi-compartment apparatus 400, in accordance with an embodiment of the present invention.

Figure 4:
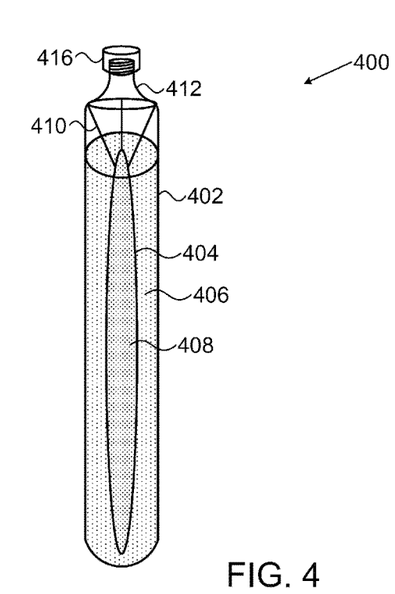
FIG. 4 is a simplified pictorial illustration of another multi-compartment apparatus, in accordance with an embodiment of the present invention.

Apparatus 400 comprises attaching means 410 for affixing an inner container 404, comprising a second liquid 408, inside an outer container 402 containing a first liquid 406. The attaching means is constructed and configured to prevent the breakage of the inner container before its intended use.

Figure 5:
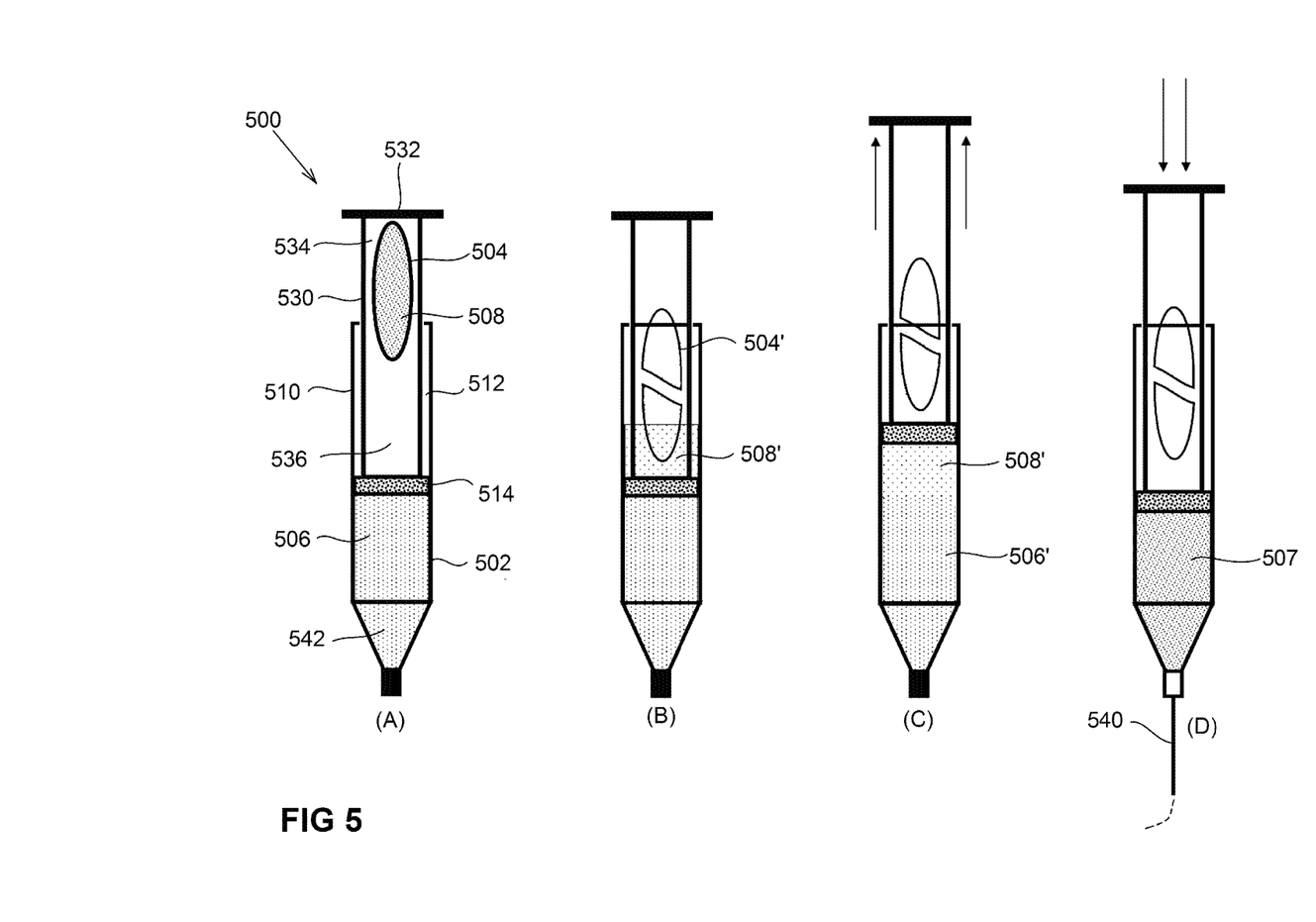
FIG. 5 is a simplified pictorial illustration of a multi-compartment syringe apparatus, in accordance with an embodiment of the present invention.

Reference is now made to FIG. 5, which is a simplified pictorial illustration of a multi-compartment syringe apparatus 100, in accordance with an embodiment of the present invention.

Multi-compartment syringe apparatus 500 is constructed and configured to enable hygienic and preferably sterile, in-situ mixing of a plurality of components before use.

According to some embodiments, apparatus 500 is for medical use for providing a medicament mixture comprising a first liquid 506 and a second liquid 508 after forming the mixture.

Multi-compartment syringe apparatus 500 comprises a plunger 530 housing a second container 504 (similar or identical to internal container 104 of FIG. 1, which contains a second liquid 508. The plunger comprises a handle section 532, an upper section 534 and a lower section 536. Plunger 530 is made of a similar or identical material to external container 102 (FIG. 1) and may also have flexible portions therein (not shown).

Multi-compartment syringe apparatus 500 further comprises a plunger receiving section 510, made out of a material similar or identical to external container 102 (FIG. 1), which comprises air 512, a filter 514 disposed below the air and above a first container 502 housing a first liquid 506. The multi-compartment syringe apparatus 500 further comprises a conical section 542 and hollow needle portion 540. Section 510 is not sealed, thereby allowing air 512 to penetrate in and out of section 510, depending on the situation of piston/filter 514. Filter/piston 514 is connected to plunger 530. The filter allows liquid passage only from first container 502 into plunger receiving section 510.

It should be noted that the surface of second container 504 is unfolded, thereby upon breaking the container, its entire content (second product) is mixed with the first product.

Figure 6:
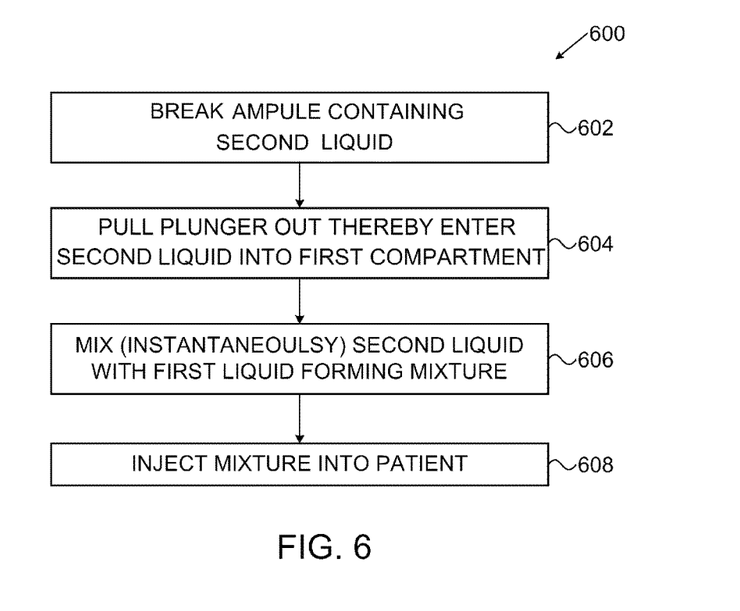
FIG. 6 is a simplified flow chart of a method for in-situ mixing of a plurality of components using the apparatus of FIG. 5, in accordance with an embodiment of the present invention.

Reference is now made to FIG. 6, which is a simplified flow chart 600 of a method for in-situ mixing of a plurality of components, prior to application using the apparatus of FIG. 5, in accordance with an embodiment of the present invention.

In a breaking step 602, scheme (A) in FIG. 5, the user breaks the inner container 504 (or ampoule) by deforming the plunger 530 such as by pressing in on flexible portion 517. This releases the second liquid 508 into the plunger. The result of this operation is illustrated in scheme (B) in FIG. 5. Reference numeral 508' denotes the spilled content 508 of container 504. Reference numeral 504' denotes the broken inner container.

In an inserting step 604, while holding syringe apparatus 500 vertically such that needle 540 turns down, the plunger is pulled out and thereby forcing the second liquid 508' to pass through the filter into first container 502, yet retaining any pieces of the broken ampoule within the plunger.

In a mixing step 606, the second liquid that has been received in first container 502 is mixed with a first liquid 506 forming a mixture (507 in FIG. 5).

In an injecting step 608 (scheme (D) in FIG. 5), the mixture is injected from the first container via the conical section and needle into the patient.

Alternatively, the mixture may be applied via needle 540 to any other suitable destination site.

Figure 7:
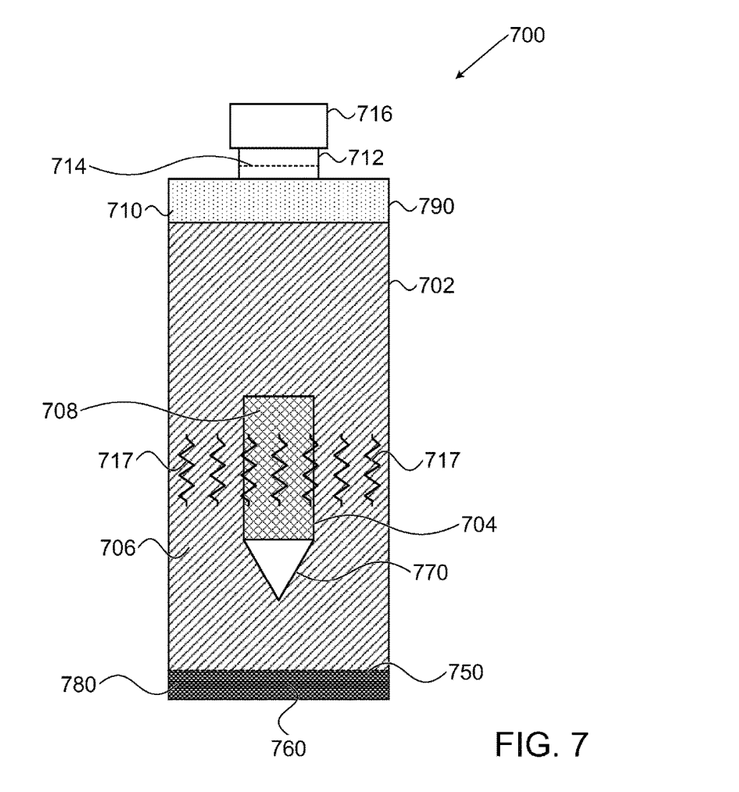
FIG. 7 is a simplified pictorial illustration of another multi-compartment apparatus, in accordance with an embodiment of the present invention.

Reference is now made to FIG. 7, which is a simplified pictorial illustration of another multi-compartment apparatus 700, in accordance with an embodiment of the present invention.

Apparatus 700 houses a solid particulate product 760 within a lower section 780. The solid particulate matter is kept dry and separate from a first liquid 706 by means of a membrane 750. The first liquid is contained within a first container 702 above the lower section of the apparatus. The first container may be constructed of a material similar or identical to first container 102 of FIG. 1. The apparatus also comprises a lid 716, a filter 714 disposed in an upper portion 712 thereof.

The apparatus may also comprise an air portion 790 comprising air 710.

A second container 704 is suspended in the first liquid. The second container comprises a second liquid 708 and a sharp pointed end section 770.

Figure 8:
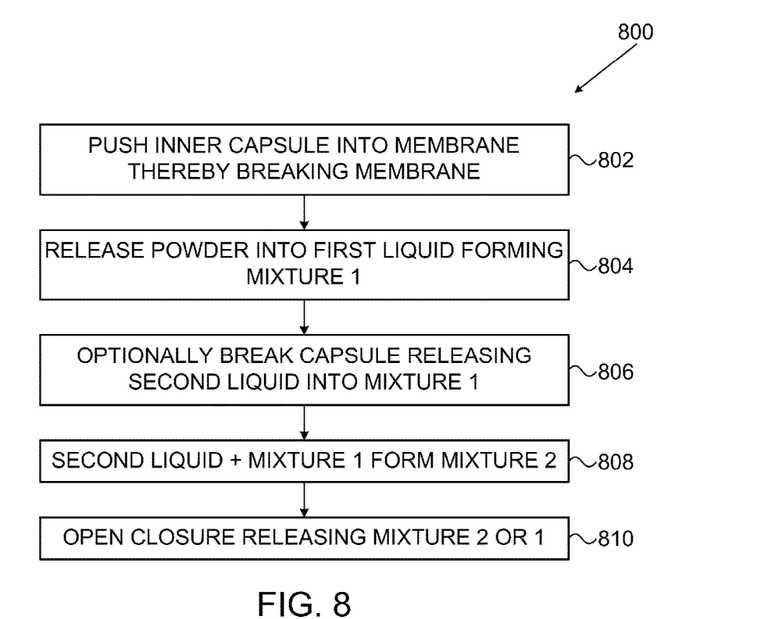
FIG. 8 is a simplified flow chart of a method for in-situ mixing of a plurality of components using the apparatus of FIG. 7, in accordance with an embodiment of the present invention.

FIG. 8 is a simplified flow chart 800 of a method for in-situ mixing of a plurality of components using the apparatus of FIG. 7, in accordance with an embodiment of the present invention.

In a membrane breaking step 802, the user pushed pointed end section into membrane 750 by, for example, pressing on the flexible section or by squeezing the first container.

Once the membrane is broken, the particulate powder product 760 is released into the first liquid, thereby forming a first mixture (not shown). This first mixing step 804 may additionally require shaking of the apparatus, in some cases.

In a second optional breaking step 806, the user breaks the second container 704 by, for example pressing on the flexible regions or bending the first container.

In a second mixing step 808, the second liquid and first mixture are mixed by diffusion and/or by shaking thereby forming a second mixture.

In a mixture application step 810, the lid is removed and the first or second mixture (depending on the previous steps) is filtered via filter 714 upon release to a destination site or container or person.

According to one embodiment, the first liquid is water, the second liquid is milk and the particulate powder is a drink powder, such as frieze-dried coffee or tea and/or sugar and/or artificial sweetener. The second mixture is thus for example, a cold coffee drink. It should be understood that the apparatus may be heated by microwave to supply a hot drink.

Figure 9:
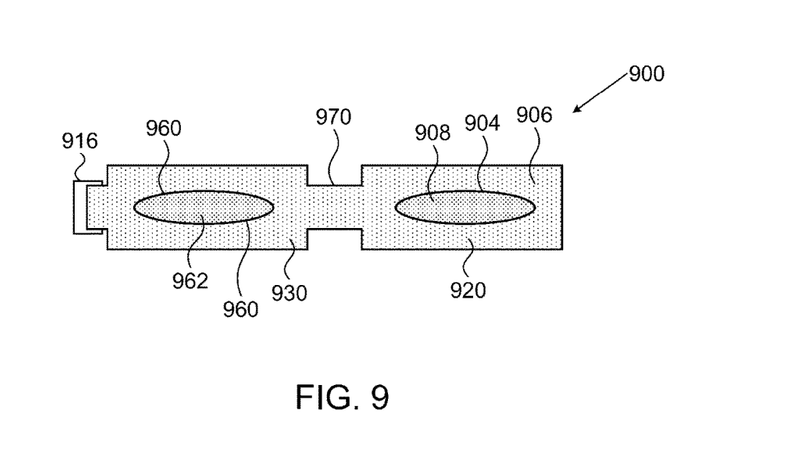
FIG. 9 is a simplified pictorial illustration of another multi-compartment apparatus, in accordance with an embodiment of the present invention.

Reference is now made to FIG. 9, which is a simplified pictorial illustration of a multi-compartment apparatus 900 for housing three liquids, in accordance with an embodiment of the present invention.

Apparatus 900 comprises a lid 916 (and filter (not shown)) a first container 902 containing a first fluid 906. Container 902 comprises two sections 920 and 930 with a narrow connecting element 970 enabling fluid connection between the two sections 920, 930. Section 920 comprises first ampoule 904 containing a second liquid 908.

Section 930 comprises a second ampoule 960 containing a third liquid 962. Ampoules 960 and 904 may be broken to release the third and second liquid into the first liquid.

Alternatively, one or more of the ampoules may contain a powder or gel or suspension. Thus, various mixtures may be made in-situ, prior to application to one or more destination sites.

The following examples are meant to provide exemplary illustrations of the present invention, which are not intended to be limiting.

EXAMPLES

Example 1

In emergency care, it is often necessary to provide a painkiller and at least one of a) an antibiotic; b) a drug and a c) vaccine. The painkillers, antibiotics, drugs and vaccines are nearly always stored separately. For example, a paramedic may need to provide a painkiller, such as lidocaine and an anti-tetanus vaccine, which can be painful. Rather than inject the patient twice, he can use the multi-compartment syringe apparatus 500 of FIG. 5 hereinabove and the method of FIG. 6, in which the lidocaine preparation is second liquid 508 and the anti-tetanus vaccine is first liquid 506.

The dosages used will be in accordance to the patient's weight, age, gender as is current practice by medical practitioners in the art.

The patient can thus be vaccinated and provided with a painkiller in the form of a mixture simultaneously.

Example 2

In emergency care, it is often necessary to provide a painkiller and at least one of a) an antibiotic; b) a drug and a c) vaccine. The painkillers, antibiotics, drugs and vaccines are nearly always stored separately. For example, a paramedic may need to provide a painkiller, such as lidocaine and an anti-coagulant, such as heparin. Rather than inject the patient twice, he can use the multi-compartment syringe apparatus 500 of FIG. 5 hereinabove and the method of FIG. 6, in which the lidocaine preparation is second liquid 508 and the heparin solution is first liquid 506.

In many other examples for medical applications, the user can use apparatus 100 of FIG. 1 comprising one medical component in the inner compartment 104 and a second medical component in the outer compartment 102. It should be further understood that the apparatus shown in FIGS. 3, 5, 7 and 9 may all be used and applied to various different medical applications.

The patient can thus be provided with an anti-coagulant and provided with a painkiller in the form of a mixture simultaneously. The dosages used will be in accordance to the patient's weight, age, gender as is current practice by medical practitioners in the art.

Many other examples in the medical field are apparent to a person skilled in the art and the example is not meant to be limiting.

Example 3

Various glues and adhesives are provided in two separate tubes, such as Epoxy or polyepoxide, which is a thermosetting polymer formed from reaction of an epoxide "resin" with polyamine "hardener". Epoxy has a wide range of applications, including fiber-reinforced plastic materials and general purpose adhesives. Apparatus 100 may be used to house an epoxy 106 and the polyamine 108 may be housed in an inner ampoule 104. Using the method of FIG. 2, the mixed epoxy may be applied to a target site, such as for bonding two pieces of metal.

Example 4

Apparatus 700 in FIG. 7 may be used to prepare coffee. According to one embodiment, the first liquid 706 is water, the second liquid 708 is milk and the particulate powder 760 is a drink powder, such as frieze-dried coffee or tea and/or sugar and/or artificial sweetener. The second mixture, produced using the method of FIG. 8 is thus for example, a cold coffee drink. It should be understood that the apparatus may be heated by microwave to supply a hot drink.

Example 5

A sportsperson may wish to drink during his/her sporting activity, such as cycling, swimming and the like. He may use the apparatus of the present invention, such as, but not limited to apparatus 100 as shown in FIG. 1. The apparatus may be a flexible or non-flexible bottle of any suitable size, such as 300 ml, 500 ml 1 liter and 1.5 liter. The outer compartment may comprise an energy gel, such as GU Energy Gel and the inner compartment an isotonic drink such as, but limited to GATORADE.

Example 6

The apparatus of the present invention shown in the figures may be used for keeping two or more beverage components stored separately, which can be mixed shortly before drinking For example, an alcoholic beverage such as Bacardi with coca cola, or vodka with energy drinks, or other kinds of cocktails. These are stored separately before use.

There are drinks without alcohol that usually contains more than one component. For example, one may wish to store soda water and tomato juice separately and mix them before use. Numerous other examples of multi-component drinks mixes may be stored separately using the apparatus of the present invention, and can then be hygienically prepared before use.

This example applies to a person who goes on a trip or on a nature hike or trek and wants to take with him his favorite drink. Applying the apparatus and methods of the present invention, this may be performed easily, whether the apparatus is made of glass, plastic or any other suitable material.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A multi-compartment syringe apparatus for in-situ mixing of a plurality of products before use, the apparatus comprising:
   a tube;
   a hollowed flexible plunger;
   a sealed breakable first container disposed in said plunger;
   a one way filter piston connected to said plunger, said piston confining a first compartment at a side of a needle of said apparatus, and a second compartment at a side of said plunger, wherein said filter allowing passage of content only from said second compartment to said first compartment, while avoiding passage of pieces of said breakable first container from said second compartment to said first compartment;
   a first product stored in said first compartment;
   a second product stored in said first sealed breakable container, thereby upon blocking said needle, breaking said first sealed breakable container and pulling said plunger out of said tube, said second product enters through said filter piston into said first compartment and mixes with said first product, and
upon unblocking said needle and pressing said plunger into said tube, said filter piston pushing the mixed products out of said apparatus, through said needle (540).

2. An apparatus according to claim 1, wherein at least one of said products is a liquid.

3. An apparatus according to claim 1, further comprising a scale, thereby enabling controlling mixed quantities.

4. An apparatus according to claim 1, wherein said first breakable container having an unfolded surface, thereby allowing exploiting the entire content thereof upon breaking.

* * * * *